US007394538B2

(12) United States Patent
Bazin

(10) Patent No.: US 7,394,538 B2
(45) Date of Patent: Jul. 1, 2008

(54) DEVICE CONFIGURED TO ENABLE A FACE TO BE OBSERVED

(75) Inventor: Roland Bazin, Bievres (FR)

(73) Assignee: L'Oreal, Paris (FR)

( * ) Notice: Subject to any disclaimer, the term of this patent is extended or adjusted under 35 U.S.C. 154(b) by 91 days.

(21) Appl. No.: 11/254,721

(22) Filed: Oct. 21, 2005

(65) Prior Publication Data

US 2006/0109342 A1 May 25, 2006

Related U.S. Application Data

(60) Provisional application No. 60/642,124, filed on Jan. 10, 2005.

(30) Foreign Application Priority Data

Oct. 22, 2004 (FR) .................................. 04 52419

(51) Int. Cl.
G01J 4/00 (2006.01)

(52) U.S. Cl. ..................................... 356/364
(58) Field of Classification Search ........................ None
See application file for complete search history.

(56) References Cited

U.S. PATENT DOCUMENTS

| 3,711,182 | A | | 1/1973 | Jasgur |
| 3,794,828 | A | | 2/1974 | Arpino |
| 4,070,096 | A | | 1/1978 | Jasgur |
| 6,728,043 | B2 | * | 4/2004 | Gruner et al. ............... 359/637 |
| 6,905,211 | B2 | * | 6/2005 | Fujita et al. .................. 353/20 |

FOREIGN PATENT DOCUMENTS

| EP | 1 433 418 A1 | 6/2004 |
| JP | A 2001-204545 | 7/2001 |

* cited by examiner

Primary Examiner—Tu T Nguyen
(74) Attorney, Agent, or Firm—Oliff & Berridge, PLC

(57) ABSTRACT

A device may include a display system including at least one of a mirror and a video system including a camera and a screen configured to return to a user positioned in front of the camera, an image acquired by the camera. The device may also include: a first polarizing system configured to polarize in a first direction light emitted by a light source; a second polarizing system configured to polarize in a second direction light received by the mirror or the camera; a mechanism configured to vary an angular offset between the first and second directions; and an angular-offset identifier system configured to identify at least three different angular offsets.

52 Claims, 3 Drawing Sheets

DEVICE CONFIGURED TO ENABLE A FACE TO BE OBSERVED

This non-provisional application claims the benefit of French Application No. 04 52419 filed on Oct. 22, 2004, and U.S. Provisional Application No. 60/642,124 filed on Jan. 10, 2005, the entire disclosures of which are incorporated herein by reference.

The present invention relates to a device configured to enable a face to be observed.

BACKGROUND

U.S. Pat. No. 3,794,828 discloses a device including a mirror, and enabling the face to be illuminated under various lighting conditions.

U.S. Pat. Nos. 3,711,182 and 4,070,096 disclose devices comprising a mirror and a lighting system using polarized light, enabling glare to be eliminated.

SUMMARY

The shine of the skin is likely to vary over the course of the day. For example, the skin may be relatively matte in the morning and shine may increase over time because of secretion of sebum or sweat, for example.

Some cosmetics, such as foundations, make it possible to reduce such shine.

However, the applied cosmetic must not completely eliminate shine, because a certain amount of residual shine is desirable to impart radiance to the complexion. The level of shine to be preserved depends not only on the nature and the complexion of the skin, but also on the desire of the consumer.

The selection of a cosmetic that makes it possible to reduce shine may thus turn out to be difficult, and a need exists to help the consumer in this choice.

A need also exists to facilitate manufacture of cosmetics, for example, foundations, as a function of the appearance, and for example, the level of shine, desired by the consumer.

Although various exemplary embodiments of the present invention may obviate one or more of the above-mentioned needs, it should be understood that some embodiments might not necessarily obviate one or more of those needs.

Exemplary embodiments of the invention may provide a device comprising: a display system comprising at least one of a mirror and a video system comprising a camera and a screen configured to return to a user positioned in front of the camera, an image acquired by the camera; a first polarizing system configured to polarize in a first direction light emitted by a light source; a second polarizing system configured to polarize in a second direction light received by the mirror or the camera; mechanical and/or electronic means for varying an angular offset between the first and second directions, the angular offset thus being modifiable; and an angular-offset identifier system configured to identify at least three different angular offsets.

According to exemplary embodiments, the user may see the effect on appearance of modifying shine, and may identify the angular offset that corresponds to the desired appearance, to the unwanted appearance, or to appearances in an acceptable range or in an unacceptable range.

In exemplary embodiments, the device may include the light source, which may optionally be secured to the display system. The light source may preferably emit diffuse light. The light source may comprise at least one of a fluorescent tube, an incandescent lamp, and a light emitting diode.

In exemplary embodiments, the device may advantageously include two light sources disposed on either side of the display system, so as to obtain more uniform lighting.

In exemplary embodiments, the light source may also surround the display system, at least in part.

For example, the light source(s) may be configured to provide lighting that closely resembles daylight. Alternatively or additionally, the light source(s) may be configured to provide some other type of lighting, for example, the incandescent lamp type.

In exemplary embodiments, one of the first and second polarizing systems may be rotary. The rotary polarizing system may be turned incrementally and/or continuously. An increment may correspond to a few degrees, for example.

In exemplary embodiments, the rotary polarizing system may be configured to turn between two extreme positions and/or to turn through a complete turn.

In exemplary embodiments, the display system may comprise a mirror. For example, the mirror may be carried by a first structure element, and the light source may be carried by a second structure element that is movable relative to the first structure element. The second structure element may be hinged onto the first structure element, for example.

For example, the first structure element and the second structure element may be configured to be folded one on the other, thereby making it easier to transport the device.

In exemplary embodiments, the mirror may optionally be circular, and may optionally be covered completely by the second polarizing system.

In exemplary embodiments, the second polarizing system may be rotary.

In exemplary embodiments, the mirror need not be rotary, and the second polarizing system may turn relative to the mirror. Alternatively, the mirror may be rotary, and the second polarizing system may turn with the mirror.

Alternatively, the second polarizing system need not be rotary, in which case the first polarizing system may be rotary, for example.

In such embodiments, for example, the first polarizing system may be of annular shape.

In exemplary embodiments, the display system need not comprise a mirror, but may comprise a video system.

In exemplary embodiments, the identifier system may comprise graduations. For example, the graduations may extend over an arc of a circle, for example, over 90° or less than 90°. The identifier system may also include an index that is configured to co-operate with the graduations. For example, the index may be defined by a drive member of the second polarizing system.

In exemplary embodiments, the identifier system may also include an angular-position sensor.

In exemplary embodiments, the identifier system may also include memory configured to store a position.

In exemplary embodiments, the device may include a display configured to display information relating to the angular offset between the first and second polarizing directions.

The device may include a camera to take a picture of the appearance selected by the user. For example, the camera may include a first polarizing system on a flash gun and a second polarizing system on a camera lens, for example, a film or digital camera configured to take still and/or moving pictures. The light source of the device may also produce the light that is required to take a picture.

Independently or in combination with the above, exemplary embodiments of the invention may provide a method of determining at least one level of shine on a face of a person, with said level of shine being selected by said person, said method comprising: enabling the face of the person to be displayed using a device comprising: a display system comprising at least one of a mirror and a video system comprising a camera in front of which the person may be positioned, and a screen configured to return to the person, the image acquired by the camera; a first polarizing system configured to polarize in a first direction light emitted by a light source, so as to illuminate the face; a second polarizing system configured to polarize light received by the display system; and means for varying the angular offset between the first and second polarizing directions, and thus varying the associated level of shine; enabling the person to modify the angular offset between the first and second polarizing directions, or to cause said angular offset to be modified, so as to enable at least one appearance to be selected; and determining the angular offset between the first and second polarizing directions, at least for said selected appearance, said offset being representative of the level of shine selected by the person.

In exemplary embodiments, the selected appearance may preferably correspond to the appearance that is desired by the person. Alternatively, the person may select an unwanted appearance, or appearances in an acceptable range or in an unacceptable range.

The angular offset determined in this way may be recorded, so as to enable the recorded angular offset to be compared with another angular offset as determined subsequently, or so as to use the recorded angular offset to prescribe a cosmetic and/or a treatment, or to prepare a cosmetic adapted to the person.

In exemplary embodiments, it may be possible to record not the angular offset itself, but information that is representative of said angular offset, for example, a level of shine or a degree of attenuation in said shine.

In exemplary embodiments, the method may be implemented when the face is made up or when not made up.

In exemplary embodiments, information concerning skin and/or hair of the person may be supplied as a function of the selected angular offset, for example, to quantify the matte look or the shine thereof.

In exemplary embodiments, a cosmetic, and/or advice about buying a cosmetic, may be supplied to the person as a function of the determined angular offset. The cosmetic may be selected from a plurality of cosmetics, for example. The cosmetics may be respectively associated with values or ranges of values that are, for example, representative of differences between selected angular offsets and an angle of 45° between the first and second polarizing directions, wherein the angle of 45° corresponds to no attenuation of and to no increase in shine.

In exemplary embodiments, the cosmetic may also be a personalized cosmetic, for example, one that is formulated in situ, for example, at a point of sale.

Independently or in combination with the above, exemplary embodiments of the invention may provide a method of demonstrating a variation in the appearance of a part of a body of a person, for example, the face, said method comprising: enabling the person to view said part of the body with a device comprising: a display system comprising at least one of a mirror and a video system comprising a camera in front of which the person may be positioned, and a screen configured to return to the person, an image acquired by the camera; a first polarizing system configured to polarize in a first direction light emitted by a light source; a second polarizing system configured to polarize in a second direction light received by the display system; and means for varying the angular offset between the first and second directions; enabling the person to modify the angular offset between the polarizing directions so as to select a first angular offset in a first time interval; enabling the person to select a second angular offset in a second time interval that is different from the first time interval; and comparing the selected first and second angular offsets, or any information that is representative of said selected angular offsets.

In exemplary embodiments, a cosmetic, for example, a foundation, may be applied to the person between the first and the second time intervals. Information may thus be supplied concerning an effect of the cosmetic as a function of the comparison, for example, the cosmetic's ability to increase the shine or matte look of the cosmetic.

For example, the first time interval may be selected to be in the morning of a given day, and the second time interval may be selected to be in the evening of the same day. This makes it possible to quantify an increase in shine over the course of the day.

Independently or in combination with the above, exemplary embodiments of the invention may provide a prescription method comprising: displaying a part of a body of a person, for example, the face, using a device comprising: a display system comprising at least one of a mirror and a video system comprising a camera in front of which the person may be positioned, and a screen configured to return an image acquired by the camera; a first polarizing system configured to polarize in a first direction light emitted by a light source; and a second polarizing system configured to polarize in a second direction light received by the display system, the orientation of the first direction relative to the second direction being modifiable; selecting a relative orientation; and prescribing a cosmetic and/or a cosmetic treatment as a function of information associated with the selected relative orientation.

For example, the selected cosmetic may act on the shine of the skin. The cosmetic may be selected from a plurality of cosmetics including different shine-controlling abilities, for example.

In exemplary embodiments, the it is also possible to determine an application characteristic for the prescribed cosmetic as a function of the selected orientation, for example, a quantity of cosmetic to be applied or regions to which said cosmetic is to be applied.

Independently or in combination with the above, exemplary embodiments of the invention may provide a method of formulating a cosmetic in which the cosmetic is formulated as a function of the angular offset determined above.

In exemplary embodiments, the method may comprise: displaying at least one part of a body of a person using a device comprising: a display system comprising at least one of a mirror and a video system comprising a camera in front of which the person may be positioned, and a screen configured to return to the person, an image acquired by the camera; a first polarizing system configured to polarize in a first direction light emitted by a light source; a second polarizing system configured to polarize in a second direction light received by the display system; and means for varying the angular offset between the first and second directions; selecting an angular offset between the first and second polarizing directions; and formulating the cosmetic as a function of information associated with the selected angular offset.

For example, in exemplary embodiments, the selected angular offset may correspond to an appearance that is desired by the person. Alternatively, the selected angular offset may correspond to an unwanted appearance, or even to appearances in a range the user finds acceptable or unacceptable.

For example, in exemplary embodiments, a shine-controlling compound or a compound imparting shine may be incorporated in the cosmetic in a proportion selected as a function of the selected orientation.

For example, in exemplary embodiments, the cosmetic may be formulated in such a manner that after the cosmetic has been applied, the desired appearance corresponds to the first and second polarizing directions being at an angular offset that is close to 45°.

Independently or in combination with the above, exemplary embodiments of the invention may provide a method of promoting the sale of a cosmetic in which at least one consumer is allowed to see at least one part of the body, for example, the face and/or the hair, using a device as defined above, and with at least two different orientations of one of the polarizing systems.

BRIEF DESCRIPTION OF THE DRAWINGS

Various details of the invention may be better understood on reading the following detailed description of non-limiting embodiments, and on examining the accompanying drawings, in which:

FIG. 1 is a diagrammatic perspective view of an exemplary device;

DETAILED DESCRIPTION OF EMBODIMENTS

Figure 2:
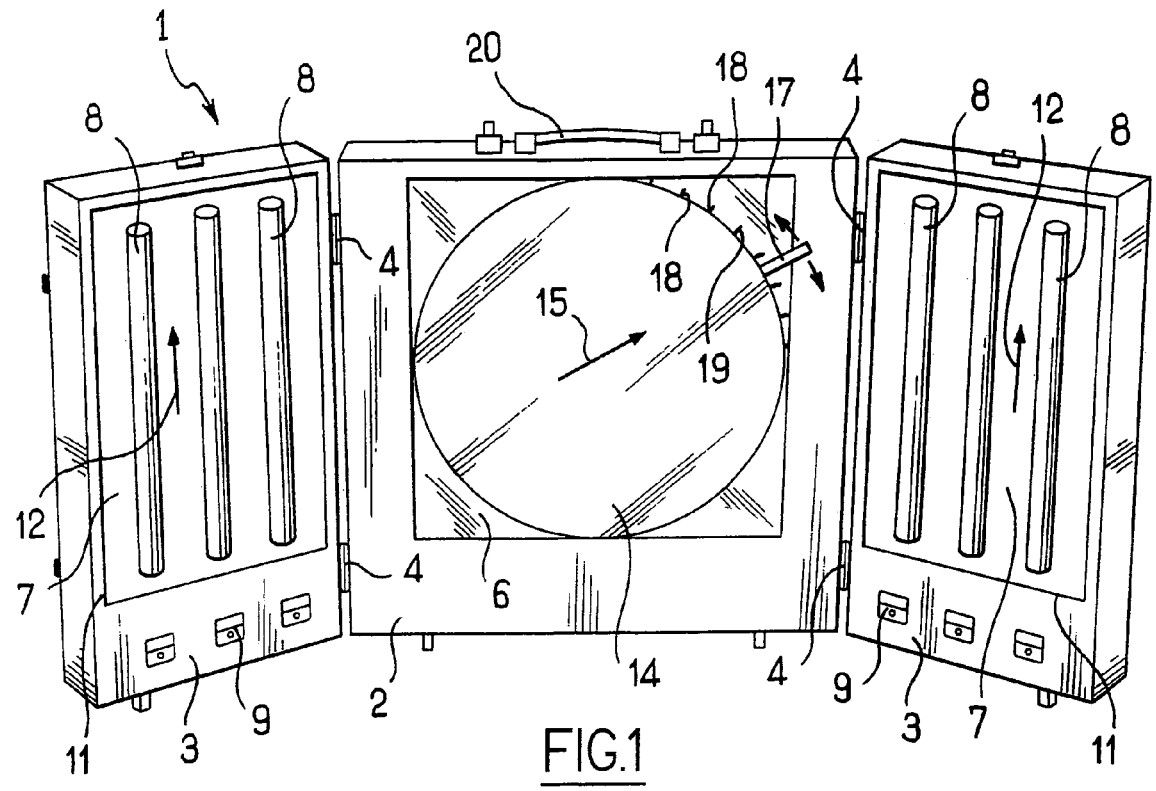
FIGS. 2 to 4 are views similar to FIG. 1 showing other exemplary embodiments.

FIG. 1 shows an exemplary device 1 in the form of a case comprising two structure elements. The first structure element may comprise a central portion 2, and the second structure element may comprise two foldable portions 3, each hinged at 4 onto the central portion 2 and forming the cover of the case.

The central portion 2 may include a display system, which, in the exemplary embodiment shown, may comprise a mirror 6 that is stationary relative to the central portion 2.

Each foldable portion 3 may include a light source 7 comprising a plurality of fluorescent tubes 8 disposed side-by-side so as to form a source of diffuse light. The tubes 8 may be placed in front of a white or reflective background of the corresponding foldable portion 3. In the exemplary embodiment shown, the device 1 may further include switches 9 that are each associated with a respective tube 8 to switch the respective tube on or off.

In use, the foldable portions 3 may be directed forward relative to the central portion 2, so as to illuminate, as much as possible, the face of a person positioned in front of the mirror 6.

The strength of each light source 7 may preferably be strong enough for the incidence of said light source on illuminating the face of the person positioned in front of the mirror 6 to be noticeable.

A first polarizing system 11 may be associated with each source 7, so as to polarize light emitted by said light source in a direction 12, which is vertical in the exemplary embodiment shown.

For example, the polarizing system 11 may comprise a polarizing film, which may be fastened onto a glass protecting the tubes 8, for example.

A second polarizing system 14 may be associated with a mirror 6, so as to polarize light in a second direction 15, which may include an orientation that is variable relative to the first direction 12.

In the exemplary embodiment shown, the second polarizing system 14 may comprise a disk of a polarizing film placed over the mirror 6, and fastened to the central portion 2 in such a manner that a middle thereof may be turned.

A drive member 17 may be configured to enable the user to cause the second polarizing system 14 to turn, so as to bring the second polarizing system 14 into a selected orientation.

Mounting the second polarizing system 14 on the central portion 2 may provide friction, so that once the second polarizing system 14 has been put in a selected orientation, the second polarizing system 14 remains in that orientation.

The second polarizing system 14 may also be mounted so as to be turnable incrementally, for example, by a cog wheel or any other mechanism that is configured to generate hard points during rotation.

In addition, an identifier system is envisaged so as to determine the orientation in which the second polarizing system 14 is placed.

For example, the identifier system may comprise graduations 18 that may be evenly distributed angularly, and that may be associated with corresponding numerical values, for example, the drive member 17 serving as an index, and the angle being read by identifying which graduation 18 is in registration with the drive member 17.

A middle graduation 19 may indicate the orientation corresponding to an angle of 45° between the polarizing directions 12 and 15.

Naturally, the invention is not limited to a particular identifier system, and graduations 18 may be replaced by other identifiers, for example, by one or more alphanumerical characters, words, graphics, for example, pictograms or colors. The term "graduation" must thus be understood broadly.

The identifier system may make it possible to identify a level of shine, for example. The term "level" should be understood as meaning a precise degree of shine or a range of degrees of shine.

Alternatively, a region of the central portion 2, for example, the mirror 6, may include an index, and the graduations or other identifiers may be on the second polarizing system 14.

Alternatively, the identifier system need not comprise graduations, but at least one sensor (not shown) configured to sense the angular position of the second polarizing system 14, for example.

The second polarizing system 14 may thus turn, for example, by a pin that drives an encoder wheel (not shown) or a potentiometer (not shown), making it possible to transform an angular movement into an electrical signal that may be processed by an appropriate electronic circuit and converted, for example, into a numerical value relating to the angular orientation, or into a more elaborate message that may can optionally be displayed on a screen or other display.

In the exemplary embodiment shown, the person who is positioned in front of the mirror 6 may cause the second polarizing system 14 to turn, so as to position said system in the desired orientation. In an exemplary embodiment not shown, rotation of the second polarizing system 14 may be motor driven, with said rotation being controlled by said person or by an operator assisting said person.

In the exemplary embodiment in FIG. 1, the case is provided with a handle 20, and if necessary or desired or desired, the case may be transported quite easily to a place where an evaluation is to be performed.

Naturally, the device 1 need not be designed to be transportable, and may be used at a fixed location.

As in the exemplary embodiment of FIG. 1, the exemplary device 1 shown in FIG. 2 may include a display system comprising a mirror. However, the display system may include a light source 7 that is annular, surrounding the display system, and may be of a shape that is different, i.e., circular.

For example, the source 7 may comprise a fluorescent tube of circular shape surrounding the mirror 6, and the first polarizing system 11, a polarizing film of annular shape, may be placed in front of the tube 8.

The second polarizing system 14 may be stationary relative to the mirror 6, and said mirror 6 may turn relative to the first polarizing system 11.

For example, the identifier system may comprise an annular part 22 surrounding the mirror 6 and on which the graduations 18 may be carried.

The mirror 6 may be secured to a drive member 23, which may also serve as an index moving in front of the graduations 18.

Figure 3:
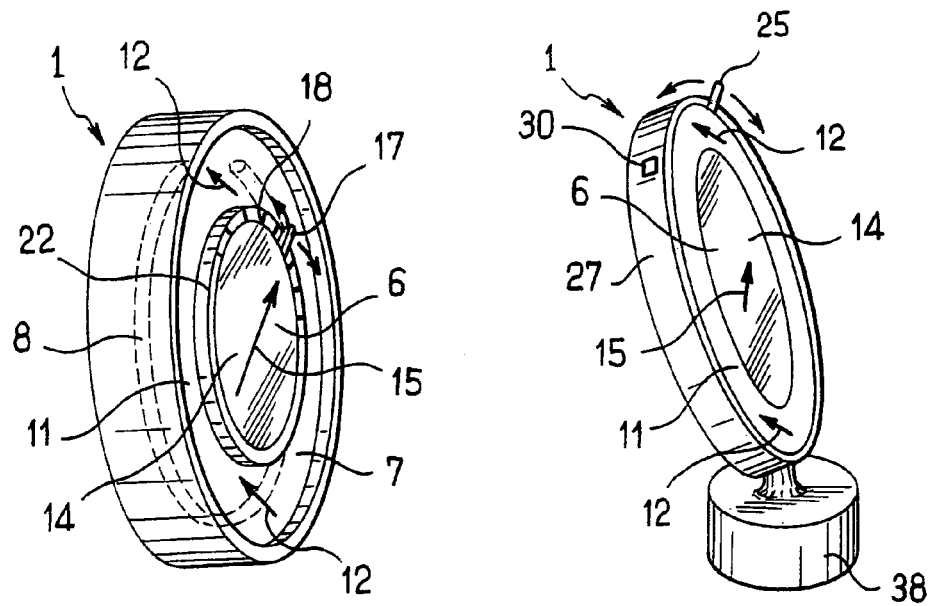

FIG. 3 illustrates the possibility of the second polarizing system 14 including a stationary polarizing direction 15, while the polarizing direction of the first polarizing system 11 may be modified.

In FIG. 3, the first polarizing system 11 may include an annular shape that may be configured to be rotated by a drive member 25 relative to the mirror 6 and a housing 27 held by a stand 28.

To identify the angular offset between the polarizing directions, the first polarizing system 11 may, for example, turn in the angular direction of the handle 25, with a cylinder (not shown) carrying graduations or other types of inscriptions appearing through a window 30 formed in the housing 27.

Thus, by looking at the graduation appearing in the window 30, the user may determine the angular position of the first polarizing system 11 relative to the second polarizing system 14.

Optical fibers (not shown) may be used to convey light between a lamp (not shown) housed in the stand 28 and the housing 27. Such optical fibers may include ends that are distributed all around the mirror 6, for example, so as to produce illumination that is uniform.

Figure 4:
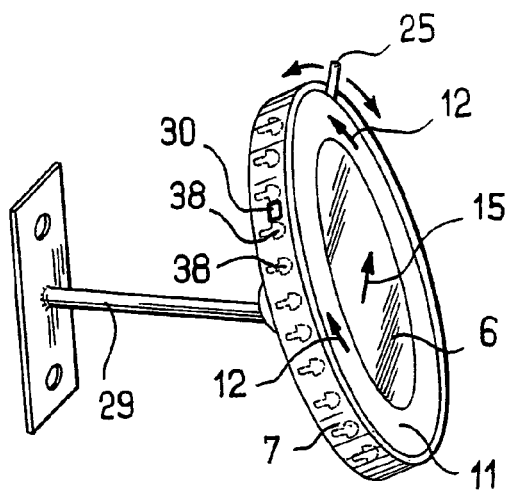

The exemplary embodiment in FIG. 4 differs from the exemplary embodiment in FIG. 3 by the fact that the stand 28 may be replaced by a wall mounting 29, and by the fact that the source 7 may comprise a plurality of light emitting diodes 38 that may be distributed all around the mirror 6 behind the first polarizing system 11, for example.

The polarizing system 6 need not include a mirror. For example, the mirror may be replaced by a video system comprising a screen 40 and a camera 41, as shown in FIGS. 5 and 6, with the image displayed on the screen 40 being the image seen by the camera 41.

Figure 5:
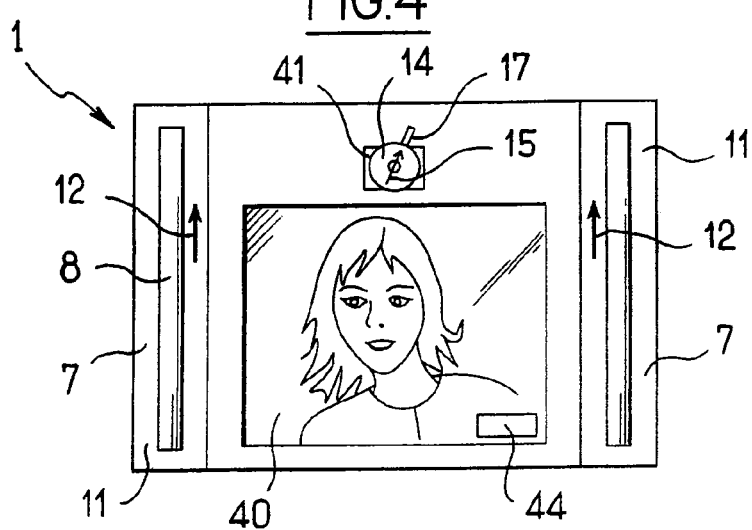
FIGS. 5 and 6 are front views of other exemplary embodiments.
Figure 6:
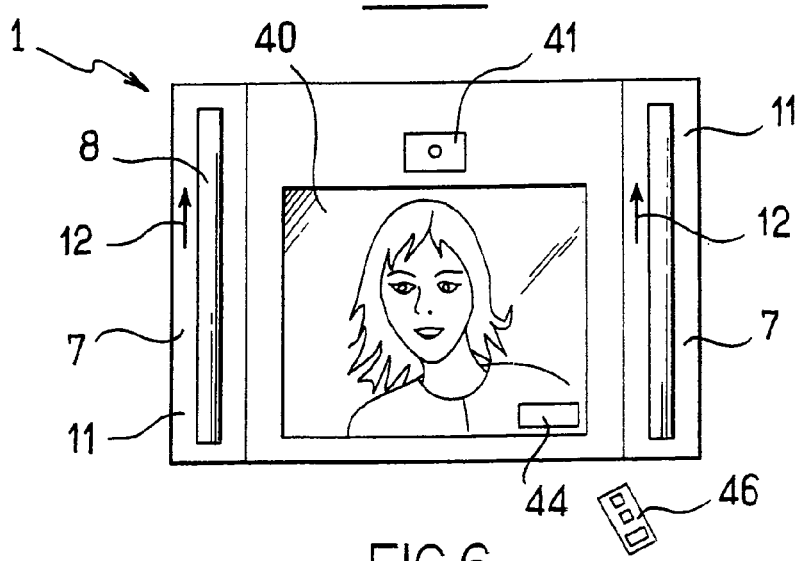

The exemplary device 1 in FIG. 5 may include two light sources 7 disposed on either side of the screen 40, with each source being provided with the first polarizing system 11.

For example, the second polarizing system 14 may be placed in front of the camera 41, so that the image appearing on the screen 40 depends on the angular offset between the polarizing directions 12 and 15.

For example, the second polarizing system 14 may be provided with the drive member 17, as in the exemplary embodiment in FIG. 1, so as to enable the user to modify the orientation of the second polarizing system 14.

For example, a position sensor may be associated with the second polarizing system 14, and information that is representative of the angular offset between the directions 12 and 15 may be displayed on the screen 40, for example, in a zone 44 thereof.

The screen 40 may be of any type, for example, a liquid crystal, plasma, or cathode ray tube (CRT) screen, with said screen being color or monochrome.

In the exemplary embodiment in FIG. 6, the second polarizing system 14 as shown in FIG. 5 may be replaced by an electronic device (not shown) configured to act directly on the camera 41.

For example, the user may control the electronic device by a remote control 46, or by any other type of interface, for example, a keyboard, a keypad, a mouse, a joystick, a touch-sensitive screen, or by voice, amongst other approaches.

Irrespective of its form, the device 1 may include means that make it possible to record an image of the person, and as seen by that person, for a given angular offset of the first and second polarizing directions 12 and 15.

In the exemplary embodiment in FIGS. 5 and 6, the image may be recorded by the camera 41, for example, with said camera 41 being configured to be connected to an image-acquisition system such as a microcomputer, for example, or any other suitable electronic device.

For the exemplary devices in FIGS. 1 to 4, or for any other exemplary embodiments including a display system that comprises a mirror, a camera may be used in association with one of the polarizing systems.

The light that is required to take a picture may come from the source(s) 7, or where appropriate or desired, from one or a plurality of flash guns, which may be provided with a polarizing system disposed so that the angular offset between the first and second polarizing directions is reproduced by the camera.

Figure 7:
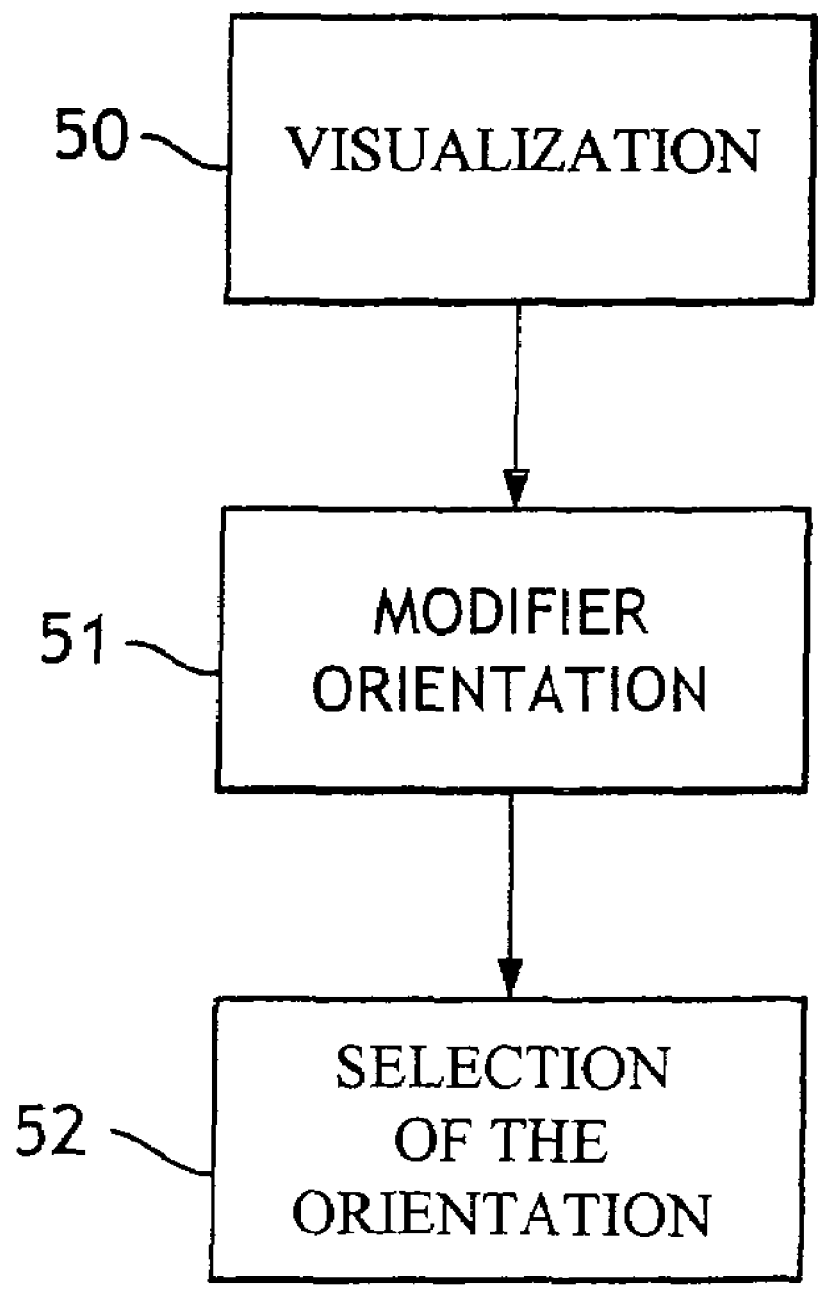
FIG. 7 is a flow chart outlining an exemplary method.

For example, an exemplary embodiment described above may be used in an exemplary selection method for selecting an appearance, as shown in FIG. 7.

In such a method, in a first step 50, a person may be positioned in front of the display system.

In step 51, the angular offset between the first and second polarizing directions may then be modified, so as to vary the image that the user can see, the image being reflected by the mirror 6, for example, or being shown on the screen 40. The user may modify the orientation, or may give instructions to another person who is responsible for operating the device on the directions of the user.

The orientation may be modified until the user decides, in step 52, that the returned appearance is satisfactory.

The identifier system may be used to identify the relative orientation of the first polarizing system. The orientation may serve as a reference, for example, and the orientations selected at different time intervals may be compared.

For example, it is possible to proceed with a first orientation selection at the start of the day, then with a second orientation selection later on in the day, and thus demonstrate variation in the shine of the skin over the course of the day.

The image corresponding to the orientation selected by the user may be treated, where appropriate or desired. For example, the treatment may include making a comparison with a real image in which the shine has not been altered by the polarizing systems. For example, it may thus be possible to determine the extent to which shine needs to be attenuated and/or the zones that need to be treated.

For example, the variation in the angle may provide information about the nature of the skin, for example, very dry skin not being very prone to an increase in shine over the course of the day.

Exemplary embodiments of the device 1 may also be useful for quantifying the effect, for example, on the shine of the skin, of the application of a cosmetic.

For example, the angular offset between the first and second polarizing directions may be identified before the cosmetic is applied, and then after application.

For example, the shine-controlling effect of a cosmetic may thus be characterized by the angle through which one of the polarizing systems turns relative to the other polarizing system between the positions corresponding to before and after application.

By performing an evaluation at the start of the day, before a cosmetic is applied, and then performing a new evaluation at the end of the day, with the cosmetic being applied in the morning after the first evaluation, it is possible to demonstrate the effect of the cosmetic, at the end of the day, on the shine of the skin, for example, to demonstrate that the cosmetic makes it possible to preserve a level of shine at the end of the day that is comparable with the level of shine at the start of the day, before the cosmetic was applied.

Exemplary embodiments of the device may facilitate formulating a cosmetic, by making it possible, for example, to determine a proportion of various components of the cosmetic that enable a predefined variation of shine between the start and the end of the day to be obtained, for example, substantially zero, and thus to prepare a cosmetic adapted to a user or to a given population.

For example, depending on the orientation selected by a person, or by a person that is representative of a population, a cosmetic may be formulated using a greater or smaller number of compounds, for example, a filler, that control shine or that impart shine.

Naturally, the invention is not limited to the embodiments described above.

In all of the exemplary embodiments shown and described, the light source may be modified, and may, for example, comprise a fluorescent tube, an incandescent lamp, or light emitting diodes, with optical fibers, where appropriate or desired, for conveying the light.

The first polarizing system may also be integrated in the light source, or said light source may emit polarized light.

The light source may also be daylight.

Where appropriate or desired, the device may comprise a source that is capable of emitting several types of light corresponding to daylight-type fluorescent or incandescent lighting, for example.

The device may be integrated in a more complex analysis system, for example, designed to inform the user about defects in the skin or about the color of the skin. The invention is not limited to evaluating shine of skin, but may also apply to shine of hair.

Throughout the description, including in the claims, the expression "comprising a" should be understood as being synonymous with the expression "comprising at least one", unless specified to the contrary.

Although various details of the present invention has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A device comprising:
   a display system comprising at least one of:
   a mirror; and
   a video system comprising a camera and a screen configured so that an image acquired by the camera is returned to a user positioned in front of the camera;
   a first polarizing system for polarizing in a first direction light emitted by a light source;
   a second polarizing system for polarizing in a second direction light received by the mirror or by the camera;
   means for varying an angular offset between the first and second directions; and
   an angular-offset identifier system configured to identify at least three different angular offsets.

2. A device according to claim 1, comprising a light source.

3. A device according to claim 2, wherein the light source is secured to the display system.

4. A device according to claim 1, comprising two light sources disposed on either side of the display system.

5. A device according to claim 1, comprising a light source that surrounds the display system, at least in part.

6. A device according to claim 1, comprising a light source that emits diffuse light.

7. A device according to claim 1, wherein one of the first and second polarizing systems is rotary.

8. A device according to claim 7, wherein a rotation of the one of the first and second polarizing systems is performed incrementally.

9. A device according to claim 7, wherein a rotation of the one of the first and second polarizing systems is performed continuously.

10. A device according to claim 7, wherein the one of the first and second polarizing systems is configured to turn between two extreme positions.

11. A device according to claim 7, wherein the one of the first and second polarizing systems is configured to be capable of turning through a complete turn.

12. A device according to claim 1, wherein the display system comprises a mirror.

13. A device according to claim 12, wherein the mirror is carried by a first structure element, and further comprising a light source that is carried by a second structure element that is movable relative to the first structure element.

14. A device according to claim 13, wherein the second structure element is hinged onto the first structure element.

15. A device according to claim 13, wherein the first structure element and the second structure element are configured to be folded one on the other.

16. A device according to claim 12, wherein the mirror is circular.

17. A device according to claim 12, wherein the second polarizing system is rotary.

18. A device according to claim 17, wherein the mirror is not rotary, and wherein the second polarizing system turns relative to the mirror.

19. A device according to claim 17, wherein the mirror is rotary, and wherein the second polarizing system turns with the mirror.

20. A device according to claim 1, wherein the first polarizing system is rotary.

21. A device according to claim 1, wherein the first polarizing system is of annular shape.

22. A device according to claim 1, wherein the display system comprises a video system.

23. A device according to claim 1, wherein the annular-offset identifier system comprises graduations.

24. A device according to claim 1, wherein the angular-offset identifier system comprises an index disposed on the second polarizing system.

25. A device according to claim 1, wherein the angular-offset identifier system comprises memory means for memorizing a position.

26. A device according to claim 1, wherein the angular-offset identifier system comprises an angular-position sensor.

27. A device according to claim 1, comprising display means for displaying information relating to the angular offset between the first and second directions.

28. A device according to claim 1, wherein the camera is capable of recording an image of a person corresponding to a selected appearance.

29. A device according to claim 28, wherein the camera comprises the first polarizing system on a flash gun and the second polarizing system on a camera lens.

30. A device comprising:
a display system comprising at least one of:
a mirror; and
a video system comprising a camera and a screen configured so that an image acquired by the camera is returned to a user positioned in front of the camera,
a first polarizing system for polarizing in a first direction light emitted by a light source;
a second polarizing system for polarizing in a second direction light received by the mirror or by the camera; wherein one of the first polarizing system and the second polarizing system is rotary relative to the other one to vary an angular offset between the first and second directions;
an angular-offset identifier system configured to identify at least three different angular offsets.

31. A method of determining at least one level of shine on a face of a person, with said level of shine being selected by said person, said method comprising:
enabling the face of the person to be displayed using a device as defined in claim 1,
enabling the person to modify the angular offset between the first and second directions, or to cause said angular offset to be modified, so as to select at least one selected appearance corresponding to a selected angular offset; and
determining the angular offset between the first and second directions, said angular offset being representative of a level of shine selected by the person.

32. A method according to claim 31, wherein the selected appearance corresponds to an appearance that is preferred by the person.

33. A method according to claim 31, wherein the person selects appearances in an acceptable range.

34. A method according to claim 31, wherein the person selects appearances in an unacceptable range.

35. A method according to claim 31, the method being implemented when the face is not made up.

36. A method according to claim 31, the method being implemented when the face is made up.

37. A method according to claim 31, wherein the selected angular offset, or information that is representative of said selected angular offset, is recorded.

38. A method according to claim 31, wherein information concerning the skin and/or the hair of the person is supplied as a function of the angular offset.

39. A method according to claim 38, wherein a cosmetic, or advice about buying a cosmetic, is supplied to the person as a function of the determined angular offset.

40. A method according to claim 39, wherein the cosmetic is selected from a plurality of existing cosmetics.

41. A method according to claim 39, wherein the existing cosmetics are associated respectively with values or ranges of values that are representative of differences between selected angular offsets and an angle of 45° between the first and second polarizing directions.

42. A method according to claim 39, wherein the cosmetic is a personalized cosmetic that is formulated in situ.

43. A method of formulating a cosmetic, comprising conducting the method of determining at least one level of shine on a face of a person according to claim 31 and formulating a cosmetic as a function of said annular offset.

44. A device according to claim 30, wherein the angular-offset identifier system comprises graduations.

45. A method of demonstrating a variation in the appearance of a part of the body of a person, as a function of time and/or of a treatment, said method comprising:
enabling the person to view said part of the body with a device as defined in claim 1,
enabling the person to modify an angular offset between the first and second directions so as to select a first angular offset corresponding to a preferred appearance in a first time interval;
enabling the person to select a second angular offset corresponding to a preferred appearance in a second time interval that is different from the first time interval; and
comparing the selected first and second angular offsets, or information that is representative of said selected angular offsets.

46. A method according to claim 45, wherein a cosmetic is applied to the person between the first and the second time intervals.

47. A method according to claim 45, wherein information is supplied concerning an effect of the cosmetic as a function of the comparison.

48. A method according to claim 45, wherein the first time interval is selected to be in the morning of a day, and the second time interval is selected to be in the evening of the same day.

49. A method according to claim 48, wherein the selected angular offset corresponds to an appearance that is preferred by the person.

50. A method according to claim 48, wherein a shine-controlling compound is incorporated in the cosmetic in a proportion selected as a function of a selected orientation.

51. A method according to claim 48, wherein a compound imparting shine is incorporated in the cosmetic in a proportion selected as a function of a selected orientation.

52. A method according to claim 51, wherein the cosmetic is a personalized cosmetic that is formulated in situ.

* * * * *